United States Patent [19]
Richard

[11] Patent Number: 5,889,278
[45] Date of Patent: Mar. 30, 1999

[54] OPTICAL COMMUNICATION DEVICE

[76] Inventor: Jenkin A. Richard, 2230 Haste, Apt. 110, Berkeley, Calif. 94704

[21] Appl. No.: 858,731

[22] Filed: May 19, 1997

Related U.S. Application Data

[62] Division of Ser. No. 444,883, May 19, 1995, Pat. No. 5,646,396.

[51] Int. Cl.⁶ .................................. H01S 3/16; H01S 3/23
[52] U.S. Cl. .................................. 250/214 R; 250/227.11; 372/9; 372/32; 359/180; 359/189; 359/195
[58] Field of Search ................................ 250/216, 201.5, 250/201.2, 201.1, 205, 214 R, 214 A, 214.1, 227.21, 227.23, 227.27, 227.11; 372/9, 22, 23, 26, 28, 29, 31, 32, 38; 356/73.1; 359/109, 190, 154, 191, 158, 195, 159, 160, 173, 180, 181, 182, 188, 189

[56] References Cited

U.S. PATENT DOCUMENTS

| | | | |
|---|---|---|---|
| 3,901,597 | 8/1975 | White | 356/4.05 |
| 4,161,752 | 7/1979 | Basilico | 358/128 |
| 4,451,914 | 5/1984 | LaBudde et al. | 369/109 |
| 4,554,836 | 11/1985 | Rudd | 73/657 |
| 5,029,023 | 7/1991 | Bearden et al. | 369/69 |
| 5,235,587 | 8/1993 | Bearden et al. | 369/106 |
| 5,260,562 | 11/1993 | Bearden et al. | 250/216 |
| 5,646,396 | 7/1997 | Richard | 250/216 |

Primary Examiner—Edward P. Westin
Assistant Examiner—John R Lee
Attorney, Agent, or Firm—Bruce H. Johnsonbaugh

[57] ABSTRACT

An optical communication device is provided. One or more pairs of matched diode lasers are located at first and second stations and are connected by a fiberoptic cable. A bit stream is applied to the output beam of the laser or lasers at the first station. The output beam carrying the bit stream passes through the fiberoptic cable to the matched laser or lasers at the second station and combine with the output beam of the receiving laser cavity at the second station to form a combined output beam. The power of the combined output beam is measured and time-dependent changes in the measured output power of the combined output beam is used to read the bit stream. Multiple pairs of matched lasers using different wavelengths may be positioned at the first and second stations. In yet another form of the invention, a frequency injection technique is utilized to modulate the output beam and a deconvolution system is provided to read the bit stream or streams.

7 Claims, 17 Drawing Sheets

OPTICAL COMMUNICATION DEVICE

This application is a division of application Ser. No. 08/444,883, filed May 19, 1995 now U.S. Pat. No. 5,646, 398.

BACKGROUND

The present invention relates in general to laser technology. More particularly, the present invention provides an apparatus and method for determining the position, speed and direction of motion of reflective targets, as well as for detecting changes in refractive indices of light transmissive gases. According to the present invention, an improved optical disc reader is provided capable of reading at relatively high speeds compared to prior art optical disc readers and/or capable of operation with extremely small pit depths. The present invention also facilitates improved transmission and reception through fiberoptic cable networks.

The prior art includes the Bearden et al U.S. Pat. No. 5,029,023 dated Jul. 2, 1991 which teaches a laser motion detector utilizing a single laser cavity and laser feedback interferometry to measure displacements in a target surface. In contrast to the teachings of the Bearden '023 patent, the present invention utilizes in one embodiment a pair of matched, monolithic diode lasers, wherein the first laser transmits an output beam and the second laser receives the reflected beam from a target. The present invention differs from Bearden '023 in several significant respects. First, the present invention utilizes in several embodiments matched diode lasers, using two or more laser cavities, wherein the output beams are easily modulated electronically. The Bearden '023 patent teaches the use of a single laser cavity which must be modulated mechanically or electro-optically and which cannot be effectively modulated electronically. Secondly, the present invention incorporates dual frequency injection to detect a target whereas Bearden '023 teaches a single frequency injection to stabilize the device (see column 7, line 53 thru column 8, line 19). Thirdly, the present invention in several embodiments includes the second harmonic as part of a compound modulated operating signal to detect the target, whereas Bearden '023 does not use harmonics in any fashion to detect the target.

The prior art also includes the Bearden et al U.S. Pat. No. 5,235,587 dated Aug. 10, 1993 which discloses a method and apparatus for storing and retrieving data from an optical disc using multiple pit depths. The Bearden '587 patent differs from the present invention in that it utilizes a single laser cavity which requires optical modulation of the beam to maintain stability. The use of a single laser cavity as taught in Bearden '587 has certain inherent problems in operating at relatively high frequencies. The primary problem is that the feedback light momentarily decreases the output power of the single laser cavity, requiring that before the next bit is retrieved, the laser must be allowed to return to its original operating power. At higher frequencies, the laser does not have adequate time to return to its original output power and would have inherent difficulty in detecting a string of zeroes, for example.

The prior art also includes Bearden et al U.S. Pat. No. 5,260,562 dated Nov. 9, 1993 which teaches a high resolution light microscope. This patent includes the same disadvantages of the other Bearden prior art summarized above.

SUMMARY OF THE INVENTION

A primary object of the present invention is to provide a system for detecting a reflective target wherein the output laser beam may be phase modulated electronically and the reflective beam is interpreted using a harmonic deconvolution scheme.

Another object of the invention is to utilize a compound modulated laser output beam which utilizes a second harmonic as part of the operating signal to detect the target.

Another object of the invention is to utilize a pair of matched lasers to detect a target, to detect motion in a target, to transmit bit streams through fiberoptic cables and to sense changes in the refractive index of gases.

A further object of the present invention is to provide a phase modulated laser output beam which has the capability of phase quadrature detection wherein the position of the target can be located within the range of $\lambda/4$.

A still further object of the invention is to provide an optical disc reader capable of reading at relatively high speeds and capable of reading shallow pit depths.

Yet another object of the invention is to provide a fiberoptic cable system capable of transmitting greatly increased bit streams between two stations in both directions simultaneously.

It is one of the purposes of the invention to measure surface motion and topography in the picometers or less and to provide a method and apparatus to simply accomplish the same.

A related purpose of the invention is to provide a system for measuring the induced phase or amplitude variations caused by a reflective or translucent material using one or more lasers.

The invention includes a method for measuring time-dependent phase or amplitude distortions which are induced for measurement reasons or data transmission and retrieval reasons. A coherent incident light beam from a stable-resonator is current modulated with a current offset. The current modulation pattern consists of one or more frequencies. In one embodiment of the device, the components of the current frequency are two sinusoidal waves f and 2f, 2f being twice the frequency of f with a phase shift.

The modulated beam is then transmitted through or reflected off the material to be studied. The beam then enters a receiving or transceiving cavity. The receiving or transceiving cavity is then optically modulated by the re-entering light. This induced optical modulation produces a fundamental for each of the components of the transmitting frequency in the intensity of the receiving cavity. The amplitude of the intensity modulation in prior art alternates between maximum and minimum peaks every $\lambda/2$ total phase change. However a strong second harmonic signal is produced when the fundamental is at a minimum. Therefore, if two frequencies are introduced at 1 MHz and 2 MHz and, if the receiving cavity intensity is filtered for 2 MHz, each component of the introduced frequency produces a fundamental and harmonics. Then at every point along the beam path the reflected light will produce a 2 MHz signal. The filtered signal is either from the fundamental of the 2 MHz or when the fundamental is at a minimum then the second harmonic of the 1 MHz is at a maximum. The second harmonic signal has an extra degree of phase shift that is introduced in the cavity, this can be compensated for by phase shifting one component of the driving signal relative to the other so that the fundamental of one and the second harmonic of the other are phase matched on the induced intensity modulation pattern. This ability to have a strong signal at all points allows for the easy use of this technology in various applications. This particular frequency modulation scheme allows for monitoring the amplitude of the feedback light.

The use of the alternating phase pattern also allows for the monitoring of the phase of the feedback signal. In another embodiment of the device, the modulating signal may be 1 MHz. The induced fundamental alternates 180° in phase every $\lambda/2$, the induced second harmonic also shifts 180° every $\lambda/2$. The two alternating patterns are shifted relative to each other by $\lambda/4$. Therefore, every $\lambda/4$ there is either a change in the phase of the fundamental or the harmonic, this allows for phase quadrature detection. For example, if each phase position were labeled relative to the driving signal or reference signal: 1-in phase, 0-out of phase, then the signal would alternate between 00,01,11, 10,00,01,11,10. . . . The amplitude of the signal could also be analyzed to further detect the exact pathlength change of the reentering light. Higher order harmonics can be used in any of the methods described.

The ability of the device to utilize resonant optical detection without the constraint of limited pathlength range also allows for data transmission by having carrier frequencies and then having a strong data modulation signal corresponding to the actual bit stream.

One general object of the invention is to provide a high speed, high density digital data storage apparatus and storage disc in the apparatus. The optical data storage disc of the invention has a substrate which defines a plurality of data storage positions, i.e. two or more. In one embodiment of the device, the disc can have multi-bit information at each data location. The data storage apparatus also can detect smaller pit depths than conventional techniques, therefore allowing the archival CD recording with lower wattage recording lasers or higher speed recording. Normally this would have the detrimental effect of not creating pits deep enough to be read. This present invention is not limited by small pit depths. The invention can also be used in magneto-optic drives to simply enhance the signal strength, similar to any optical amplifier, with ideal polarization qualities.

Also disclosed is a method of retrieving digital information. In the method, a focused laser beam is directed onto the surface of the optical data disc, of any number of formats, and a portion of the light is reflected back into the same laser or another laser using the modulation scheme described and which causes an intensity change in the laser that is detected and converted into a bit stream. Because of the stronger signal detection method, the disc can be read at a significantly higher speed. More than two lasers may also be used in this modulation scheme. For example, there may be more than one transmitting laser or more than one receiving laser, each modulated or filtered independently.

This technique also has the advantage of having a specific depth of field. Therefore information can be stacked at different optical layers and the information can be read at these different layers by focusing through the top layers to retrieve information at the lower layers. This allows an enormous amount of information to be stored on a disc. The layers can also be frequency separated. As the retro-reflected light is only amplified if it is within the gain curve of the laser, multiple wavelengths can be used. For example, different layers may have photoabsorbant pits for different wavelengths, allowing for easy multi-layer scanning. Due to the increased sensitivity of the method, standard photoabsorptive material could easily be detected. The apparatus can operate with or without the optics that are used in prior art for optical disc detection.

The invention can be used to examine surface features of a target. The position dependent variation can be either a phase or an amplitude variation.

The present invention may be used for retrieving information from position-dependent surface displacements by moving the incident beam to selected positions on the target or for moving the target to place the beam on selected portions of the target.

In still another embodiment, the method is used for data transmission and reception. A fiber optic is used to couple two lasers with matching gain curves or is used to couple a laser and an optical phase modulator. The harmonic deconvolution scheme is then used to generate a continuous operating region, i.e., using f and 2f. A bit stream is then superimposed upon the carrier modulation signal. In the two laser configuration, both the lasers can act as transmitters or receivers. In the one laser design, light is transmitted through a fiber into an optical path length modulator, the light is then reflected back into the fiber and subsequently into the laser for amplification and detection. In this particular configuration, the optical modulator is the transmitter of the bit stream and the laser is the detector. One of the current limitations in the resonant optical amplification configurations of the prior art is the existence of inoperable regions of the phase matching curve; this is not a limitation of this invention. One of the invention's primary advantages lies in its ability to convert phase modulation to intensity modulation without complex optical elements. This allows for the use of rapid phase modulation which has the potential for higher bit rates than intensity modulation. But because of the ability to also use intensity modulation, this technique has increased versatility.

In still another embodiment, the method is used for fiberoptic transmission using wavelength division multiplexing and frequency division multiplexing. Due to the inherent frequency selectivity of the resonant cavity, the invention allows for the modulation and transmission of multiple wavelengths and the independent detection of each of the wavelengths and their respective bit streams. This has great potential for gigabit networks, where the primary limitation is the cost of the wavelength division due to complex optics and alignment. The invention in another aspect can be used to transmit bit streams with each temporal modulation or position corresponding to more than one bit. For example, instead of transmitting the bit streams based on a binary format, the signal can be transmitted with a base number of three. This is possible due to the multiple position phase detection abilities of the device. The device can also conveniently be used with non-monolithic lasers in spite of the intensity losses of the inserted optics due to the optical amplification of the invention.

The invention can also be used to measure the frequency and amplitude of vibrations of a target. The amplitude of the vibration is determined from the time dependent variations in the power level measured by the light intensity detector and the frequency is determined from the frequency of the time-dependent variations and the power level. The invention may be used to provide a highly sensitive microphone. The invention has significant advantages over conventional techniques because no phase distortion is introduced in the audio spectrum by the transducer. Using an optical transducer also allows for large area detection. For example, the transmitting laser is coupled to a beam expander with a large beam waist, allowing motion detection over a large area. This allows for the ability to cancel Brownian motion noise due to the high sensitivity of the laser feedback technique.

In still another embodiment, the invention is used to provide an instrument capable of measuring change in position or distance while keeping track of information bidirectionally to nanometer scale accuracy. This is done by quadrature detection of the intensity and phase signal of the laser. The phase logic states are divided into four distinct states, which can then be stored and the direction of the target surface can then be determined by the next relative state. For example, if the target surface is currently in a position corresponding to the phase state "00" and the next state is "01" or "10," the target surface can be said to have moved forward or backward, respectively. Accuracy can be improved by including additional optical reflections between the control unit and the target, as this would multiply the induced path length change caused by the motion of the target surface. The accuracy could also be increased by coupling the quadrature detection with the harmonic intensity analysis.

The measurement of change in position of the target surface can also be analyzed for its rate of change, thereby being able to determine the speed of motion of a target. This embodiment of the invention, a velocimeter, is able to operate using scattered light and non-reflective targets, giving it great versatility.

In still another embodiment, the method is used for the detection of vapor or liquid density. Due to the change in the effective refractive index of a medium, the invention can detect changes in density or composition. For example, the transmitted beam passes through a chemical vapor chamber, and the light reenters the receiving or transceiving laser cavity. In this configuration, the vapor density in the chamber directly modulates the phase and intensity of the feedback light allowing for direct density measurement using the method. Accuracy can be increased by increasing the pathlength through the vapor chamber. Chemical composition can also be detected by use of specific wavelengths and appropriately extrapolating the induced phase modulation pattern for each of the appropriate wavelengths and determining a unique phase fingerprint.

Further objects and advantages of the invention will become apparent from the following description and the drawings wherein:

DETAILED DESCRIPTION OF THE DRAWINGS

Figure 1:
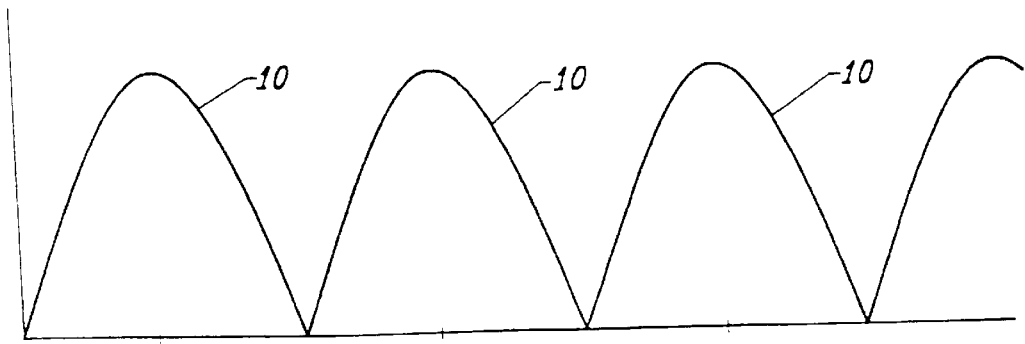
FIG. 1 is a schematic representation of a fundamental envelope known in the prior art.
Figure 2:
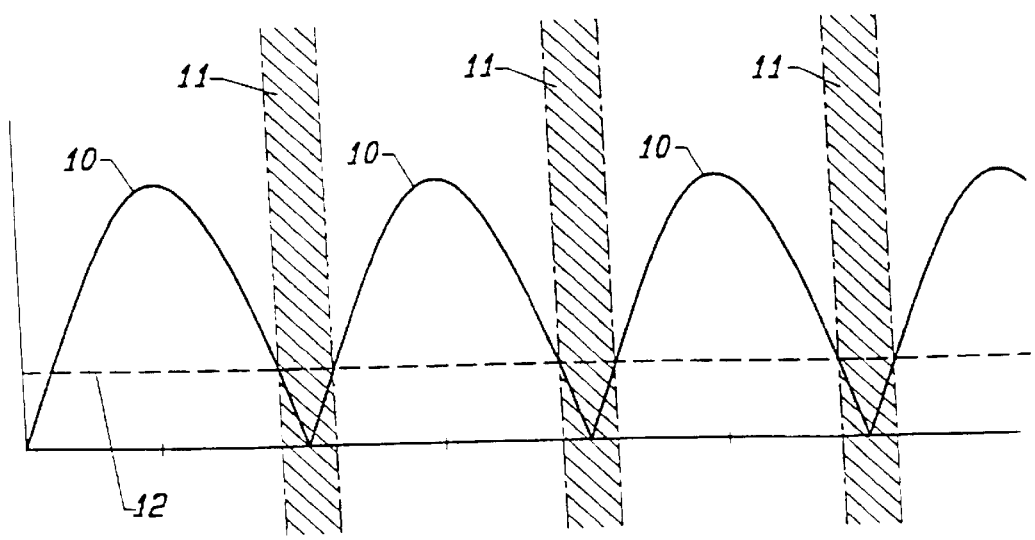
FIG. 2 is a schematic representation of the fundamental envelope of FIG. 1 known in the prior art wherein the non-operating regions are highlighted.

FIGS. 1 and 2 show the fundamental envelope 10 known in the prior art. Envelope 10 is generated in a laser receiving cavity. The peaks of the envelope shown in FIGS. 1 and 2 represent absolute values, and the horizontal axis of FIGS. 1 and 2 represents the distance of a mirror or reflective surface from a laser output.

Referring to FIG. 2 regions 11 are highlighted which represent regions of relatively low intensity feedback signal strength of a laser output beam reflected back from a target into a laser receiving cavity. The laser detection systems of the prior art are essentially inoperable within regions 11 because of the weakness of the feedback signal. The dotted horizontal line 12 of FIG. 2 represents the feedback signal threshold amplitude below which the feedback is insufficient to create a reliable and useful signal.

Figure 3A:
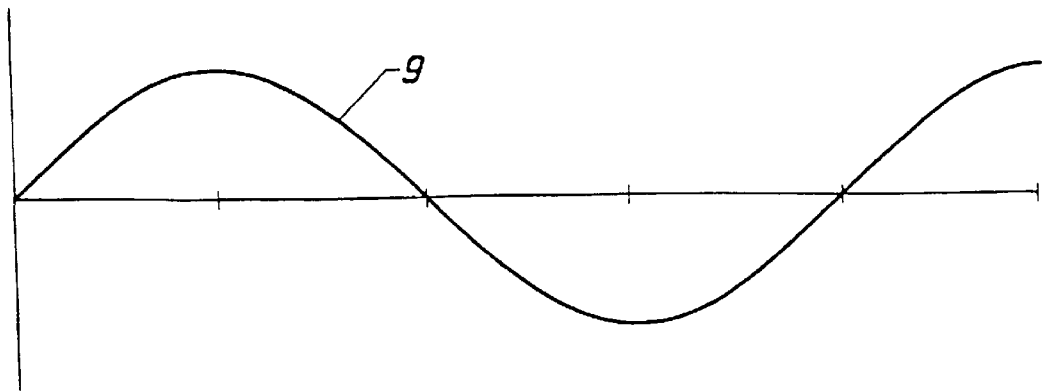
FIG. 3A is a schematic representation of a light wave.
Figure 3B:
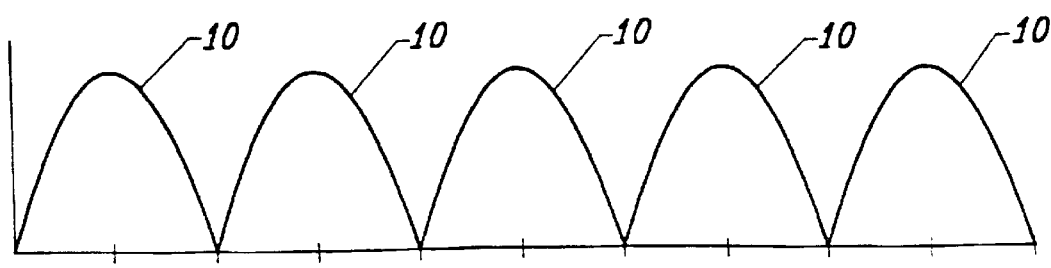
FIG. 3B is a schematic representation of a fundamental envelope.
Figure 3C:
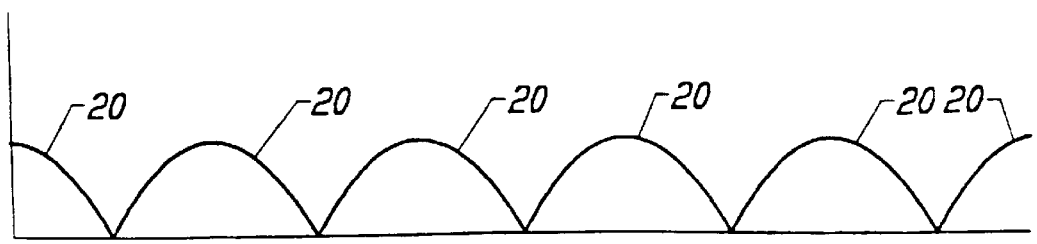
FIG. 3C is a schematic representation of the second harmonic envelope generated along with the fundamental envelope of FIG. 3B.
Figure 4:
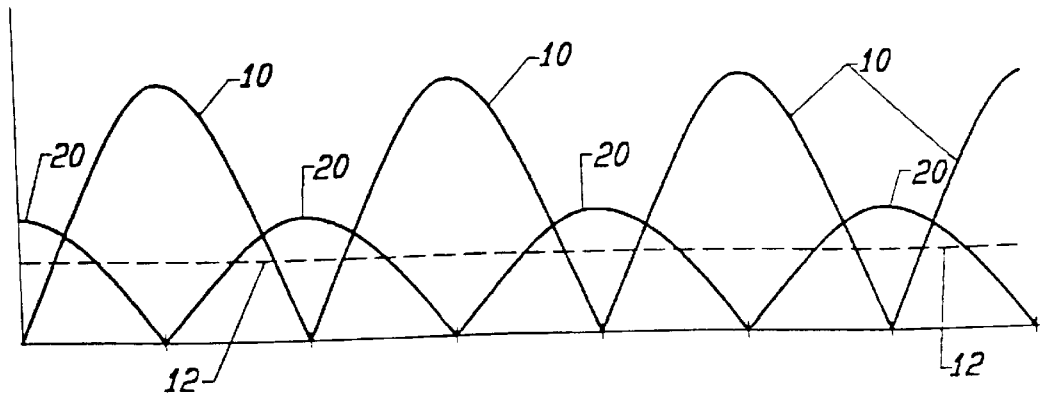
FIG. 4 is a schematic representation of the compound modulated beam according to the present invention showing a fundamental envelope and a second harmonic envelope.
Figure 5:
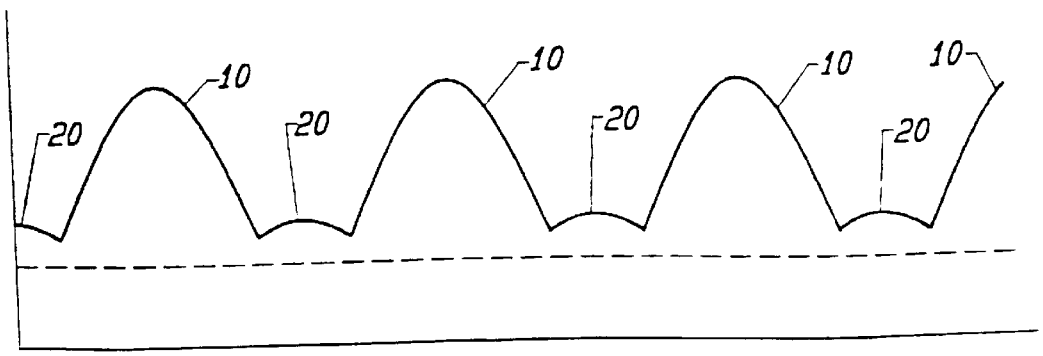
FIG. 5 is a schematic representation of the operating portions of the compound modulated beam according to the present invention.

FIGS. 3–5 represent schematically how one embodiment of the present invention provides a compound modulated beam which avoids the inoperable regions experienced by the prior art as shown in FIG. 2. FIG. 3A schematically represents the wave form of a typical laser output beam having a wavelength λ of typically 780 nanometers. FIG. 3B represents the fundamental envelope 10 within which the output beam of FIG. 3A oscillates, showing absolute value along the vertical axis and along the horizontal axis distance from the laser output to a reflective target or mirror surface.

FIG. 3C represents a second harmonic envelope 20 generated by the wave 9 from FIG. 3A as the fundamental envelope 10 of FIG. 3B is created.

A significant aspect of the present invention is shown schematically in FIG. 4 wherein the fundamental envelope 10 is shown together with the second harmonic envelope 20. According to the present invention, a laser output beam is modulated in such fashion that the fundamental envelope 10 of a first modulating wave $f_1$ is combined with the second harmonic 20 of a second wave $f_2$ and in the receiving laser cavity the feedback signal utilized includes portions of the fundamental envelope and portions from the second harmonic envelope shown in FIG. 4. This feedback signal remains at an intensity level greater than that represented by threshold 12 in FIG. 4 irrespective of the path length between the output laser to the target and back into the receiving cavity.

FIG. 5 is a schematic representation of the feedback signal utilized according to the present invention wherein the intensity level remains above the threshold level 12 irrespective of path length.

Figure 7:
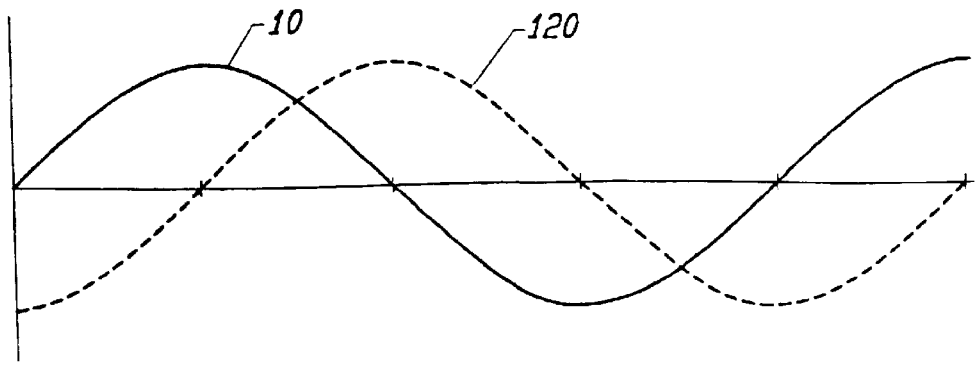
FIG. 7 is a schematic representation of the phase changes of the compound modulated beam utilized in the present invention.

The feedback signal represented in FIG. 5 can be generated using either a single wave $f_1$ or by using the fundamental of a first wave $f_1$ and the second harmonic of a second wave $f_2$. The amplitude of the second harmonic can be increased to flatten the feedback signal by simply increasing the amplitude of wave $f_2$ to the point where its amplitude is twice that of the wave $f_1$. In that case, the amplitude of the second harmonic 120, as shown in FIG. 7, would be as great as the fundamental 10 of $f_1$ shown in FIG. 7.

As used herein and in the claims, the phrase "beam modulation means" includes frequency and/or amplitude modulation. The phrase also includes direct current modulation or optical pathlength modulation. The preferred form is direct current modulation of a diode laser, as shown for example in FIG. 21. Although the preferred embodiment utilizes different frequencies for waves $f_1$ and $f_2$, a single frequency can be used wherein $f_1=f_2$.

In accordance with the present invention, deconvolution means are provided to filter the fundamental 10 of wave $f_1$ and the second harmonic 20 of wave $f_2$. Although other harmonics may be utilized, in the preferred embodiment the second harmonic is the preferred harmonic. The deconvolution means includes commercially available, standard filters for separating the fundamental of wave $f_1$ and the second harmonic of wave $f_2$.

Figure 6:
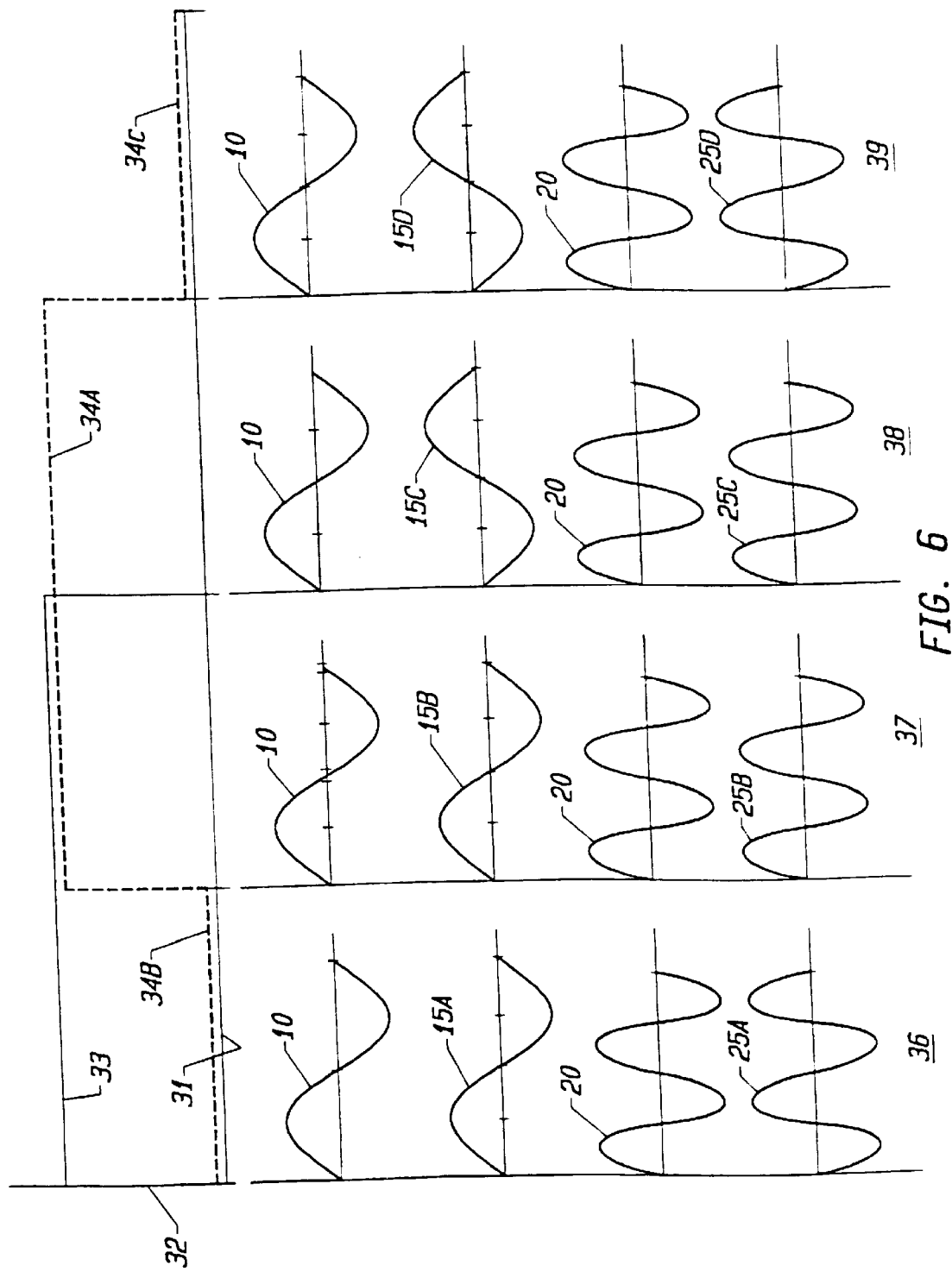
FIG. 6 is a schematic representation of the phase quadrature detection scheme of the present invention.

FIG. 6 is a schematic representation of the phase quadrature detection system according to the present invention. As shown in FIG. 6, the reference fundamental 10 is generated and a reference harmonic 20 is generated. The fundamental patterns inside the laser receiving cavity of the present invention are shown as 15a,15b,15c and 15d. The second harmonic being generated inside the receiving cavity is represented as 25a,25b,25c and 25d. The upper graph of FIG. 6 represents on the horizontal axis 31 the four quadrants of a given wavelength and the vertical axis 32 represents the presence of a signal when the reference fundamental 10 is in phase with the fundamental inside the receiving cavity, i.e. 15a,15b,15c or 15d. In the first quadrant represented by reference numeral 36, the fundamental 10 is in phase with fundamental 15a in the receiving cavity and therefore a positive signal, shown by the solid line 33, is detected in quadrant 36. The reference harmonic 20 in first quadrant 36 is inverted or out of phase with the harmonic 25a inside the laser receiving cavity and therefore no signal is detected as indicated by 34b. Therefore, in first quadrant 36, the fundamental is in phase and can be represented by a "1," the second harmonic is out of phase, no signal is generated and that condition can be represented by a "0." In the second quadrant 37, the reference fundamental 10 is again in phase with the receiving cavity fundamental 15b, the signal as shown as 33 in quadrant 37 is again positive and may be represented by a "1." In quadrant 37, the reference harmonic 20 is in phase with the harmonic inside the receiving cavity 25b and the signal 34a is positive which may be represented by a "1." In third quadrant 38, the fundamental 10 is out of phase with the fundamental inside the receiving cavity 15c, the signal 33 shifts to the "0" position shown in FIG. 6 and may be represented by a "0." The reference harmonic 20 is in phase with the harmonic inside the receiving cavity, as shown by 25c, the signal 34a remains positive which may be represented by a "1." In the fourth quadrant 39, the fundamental is out of phase with the receiving cavity fundamental 15d and the reference harmonic 20 is out of phase with the harmonic inside the receiving cavity, as shown by 25d, both of which are conveniently represented by "0." These relative phase shifts of 180° of either the fundamental or the second harmonic produce four distinct logic states as represented in FIG. 6 and which may be represented in digital format as 1,0; 1,1; 0,1; and 00 for each of the four quadrants. The presence of these four distinct logic states represented by the presence or absence of phase inversion between the fundamental and the second harmonic facilitates the use of "phase quadrature detection."

Figure 8:
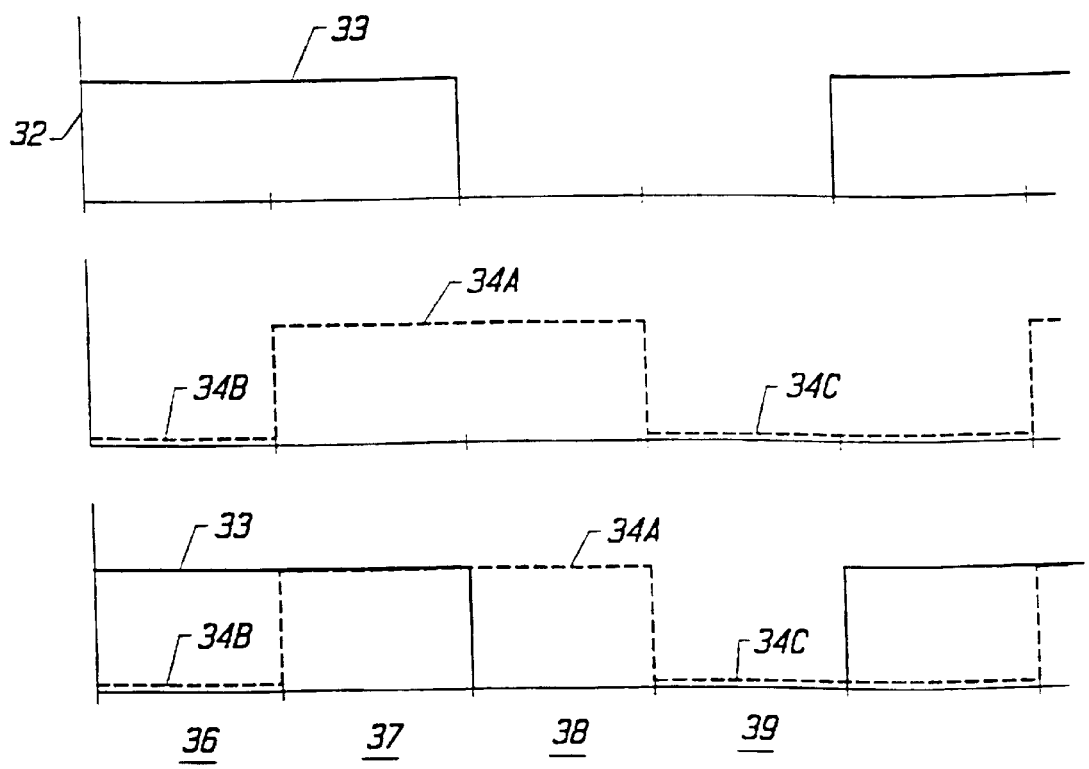
FIG. 8 is a schematic representation of the phase quadrature detection according to the present invention.

FIGS. 7 and 8 are schematic representations which illustrate the phase quadrature detection system of the present invention. FIG. 7 illustrates an alternate embodiment wherein the fundamental envelope represented by 10 and the second harmonic envelope is shown by 120. The second harmonic envelope 120 is of the same amplitude as that of the fundamental 10 which in effect produces a "flat" feedback signal which is strong in amplitude regardless of path length. This combination of feedback signals can be used in a second embodiment of the present invention wherein amplitude modulation is used for target detection.

FIG. 8 is a schematic representation showing the phase quadrature detection scheme and four distinct logic states occurring in quadrants 36 thru 39. FIG. 8 shows the upper graph of FIG. 6 in greater detail.

Figure 9:
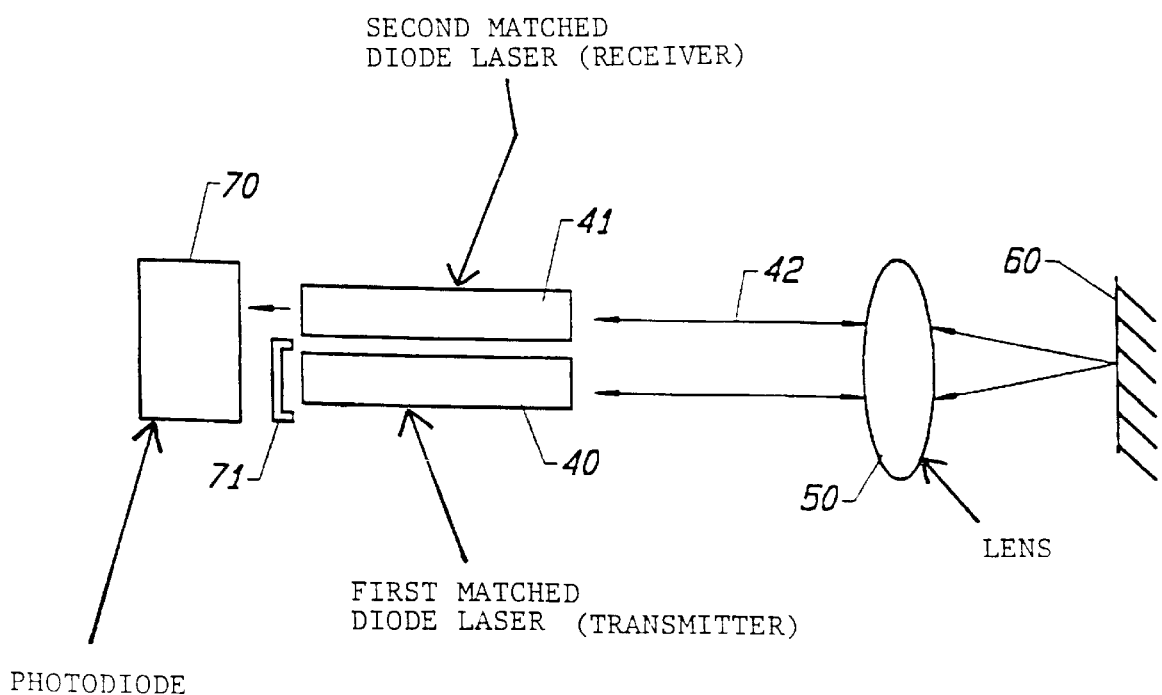
FIG. 9 is a schematic showing of one embodiment of the invention utilizing matched diode lasers used to detect motion or surface changes in a reflective target.

FIG. 9 represents a schematic diagram of a preferred embodiment of the present invention. This embodiment shows a pair of "matched" diode lasers 40 and 41. These lasers may be obtained from SDL Inc. in San Jose, Calif. as Model Nos. SDL-5601-V1. These are dual beam separately addressable high power laser diodes. The lasers 40 and 41 are monolithic, in that they are made from the same substrate material and both are stable-resonator lasers. The first matched laser 40, as shown in FIG. 9, is a transmitting laser, the output of which is focused by lens 50 onto a reflective target surface 60. The reflected beam passes back through lens 50 into the second matched laser 41. The output of the receiving laser cavity 41 is transmitted to a photodiode 70 which measures the output power of the receiving laser cavity 41.

According to one aspect of this invention, a light block 71 is mounted between the first matched laser 40 and photodiode 70 to prevent the output from transmitting laser 40 from entering photodiode 70. The presence of light block 71 in the overall arrangement shown in FIG. 9 adds considerably to the overall sensitivity of the system.

Figure 17A:
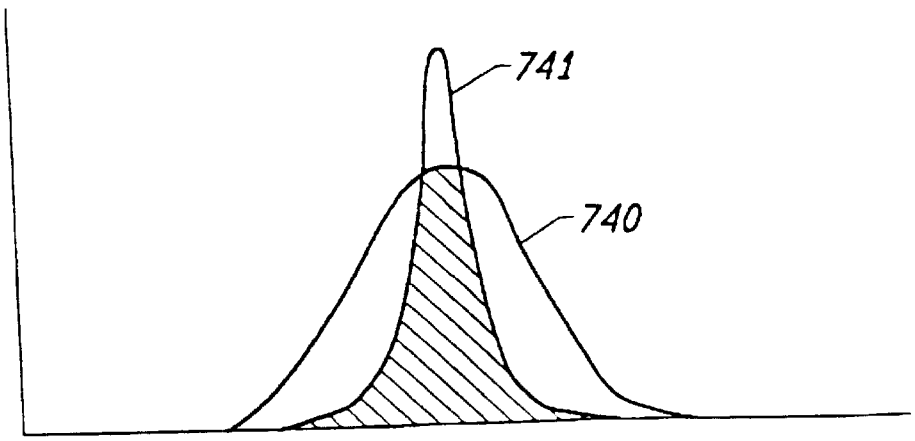
FIGS. 17A, 17B and 17C are line width curves of transmitting and receiving matched lasers according to the present invention.
Figure 17B:
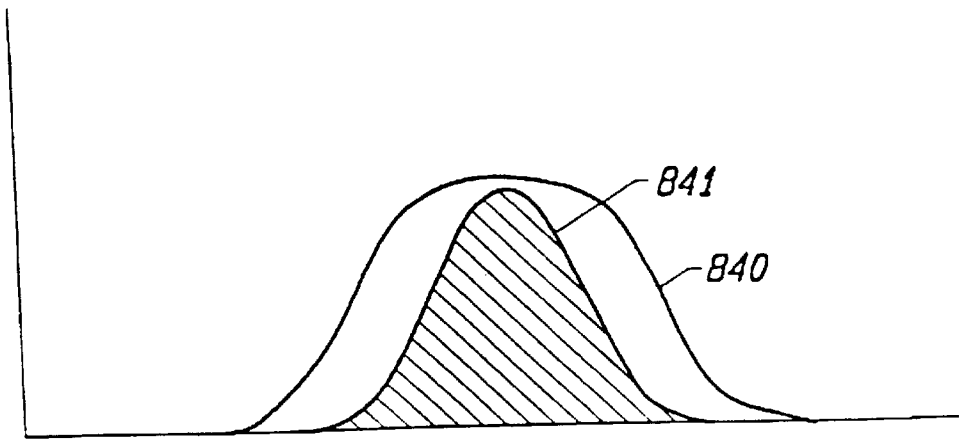
Figure 17C:
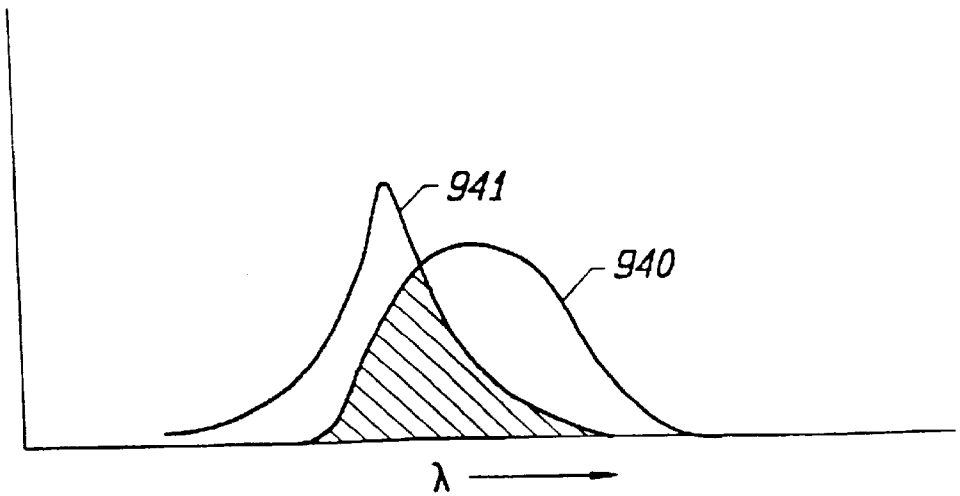

As used herein, and in the claims, the phase "matched lasers" refers to two or more lasers having line width curves which overlap to a sufficient degree wherein each of the matched lasers is capable of operating at a wavelength at which the other matched laser or lasers are capable of operating. FIGS. 17A–17C show line width curves for three pairs of "matched lasers" 740 and 741, 840 and 841 and 940 and 941. The shaded areas represent common operating regions or overlap of each pair of matched lasers. In certain applications of the arrangements shown in FIG. 9, the reflected beam 42 entering the receiving laser cavity 41 will cause resonant optical amplification in the receiving cavity and cause amplification of the feedback signal. The amplification allows the system of FIG. 9 to operate with higher speeds of motion of the reflective target 60.

The system represented in FIG. 9 may be used with or without the compound modulated beam illustrated in FIG. 5. In the preferred embodiment of the invention, the compound modulated beam would be utilized in the system of FIG. 9. The waves of frequency $f_1$ and $f_2$ are electronically modulated onto the output beam of laser 40 (also sometimes referred to herein as "frequency injection") by the use of well-known commercially available electronic signal generators. The system represented in FIG. 9 may also be operated without compound modulated beam pattern as represented in FIG. 5.

The photodiode 70 forms a means for measuring the power of the output beam of receiving laser cavity 41. Photodiode 70 may be an EE&G SGD 100-A silicon photodiode.

Figure 23:
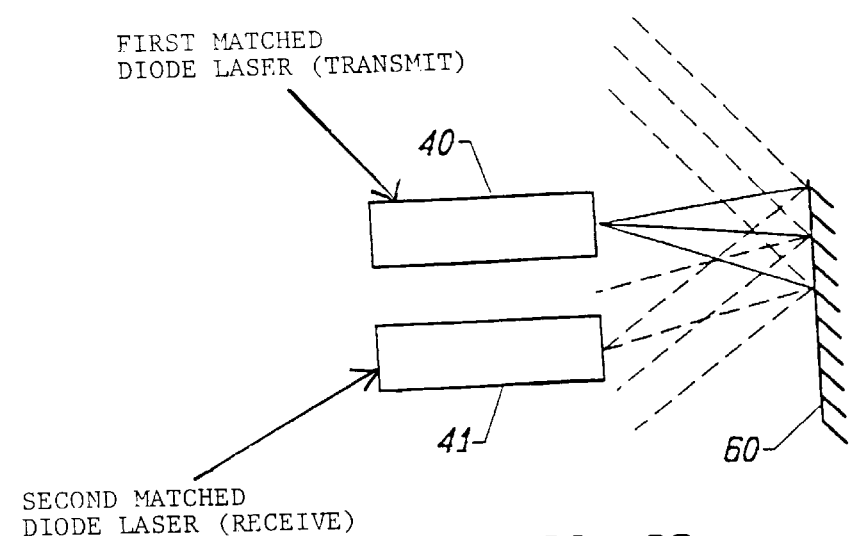
FIG. 23 is a schematic representation illustrating how the present invention may be used in conjunction with matched diode lasers, without a photodiode and without a focusing lens.

Alternately, as shown in FIG. 23, instead of using a photodiode, the impedance of a receiving diode laser may be measured. The system of FIG. 23 does not require a lens.

Deconvolution means 80 is connected to the photodiode 70 and uses commercially available electronic filters for filtering the fundamental frequency of wave $f_1$ and the second harmonic of wave 2 (or other particular harmonic being utilized).

Figure 10A:
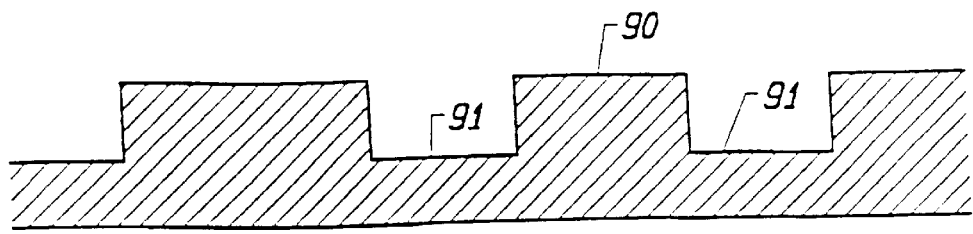
FIGS. 10A, 10B and 10C are sectional views of three optical discs; 10A shows prior art pit depths, 10B shows shallow pit depths which may be used according to the present invention, and 10C shows multi-pit depths which are capable of storing multiple pieces of information which also may be used in conjunction with the present invention.
Figure 10B:
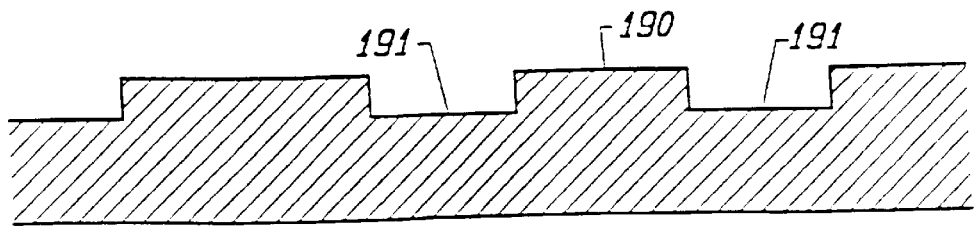

FIG. 10 represents cavities or pits which are typically utilized in optical and video discs, including CD ROMs. Disc 90 is shown having a plurality of pits 91 having a uniform depth d. FIG. 10B shows an alternate disc substrate 190 having shallow pits 191 of uniform depth d which may be utilized according to the present invention with a system such as illustrated in FIG. 9. The pits which may be used in conjunction with the optical reader illustrated in FIG. 9 can be less than 100 nanometers.

Figure 10C:
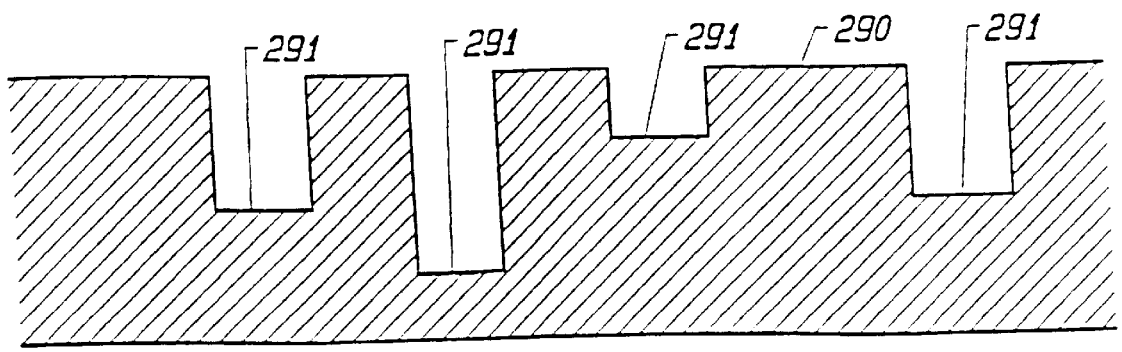

In another aspect of the present invention, the alternate disc design, shown in FIG. 10C, utilizes a substrate 290 having pits 291 of varying depths capable of storing multiple bits of information. In one aspect of the present invention, the multiple pit depths, shown in FIG. 10C, are read by the matched laser configuration illustrated in FIG. 9. The preferred embodiment of the optical reader illustrated in FIG. 9 used with the multi-pit disc illustrated in FIG. 10C would utilize the "frequency injection" technique of introducing a first wave f1 and a second wave $f_2$. An optical reader of such configuration would be capable of operating at much higher frequencies than the prior art Bearden optical reader because the present invention utilizes separate transmitting and receiving laser cavities, which configuration is inherently capable of operating at much greater speeds than the Bearden single cavity configuration.

Figure 11A:
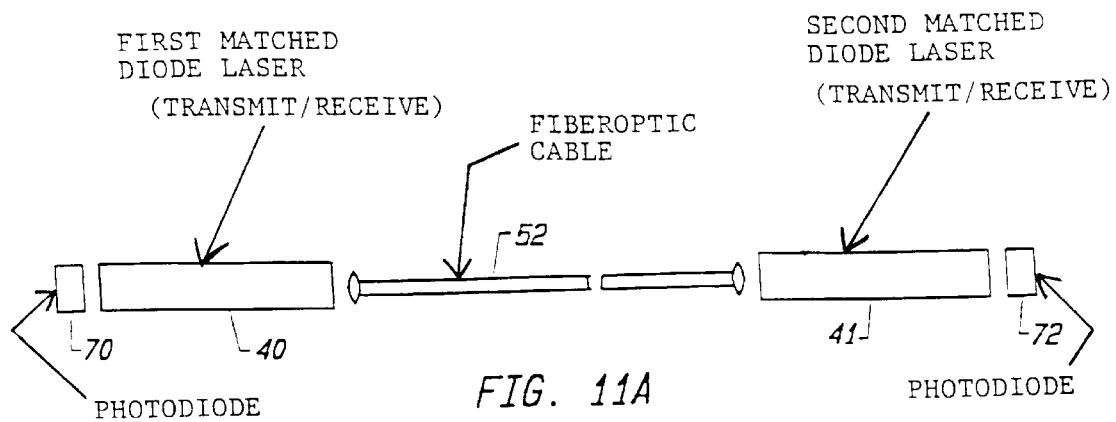
FIG. 11A is a schematic representation of matched lasers coupled by a fiberoptic cable which may be used in conjunction with the present invention.
Figure 11B:
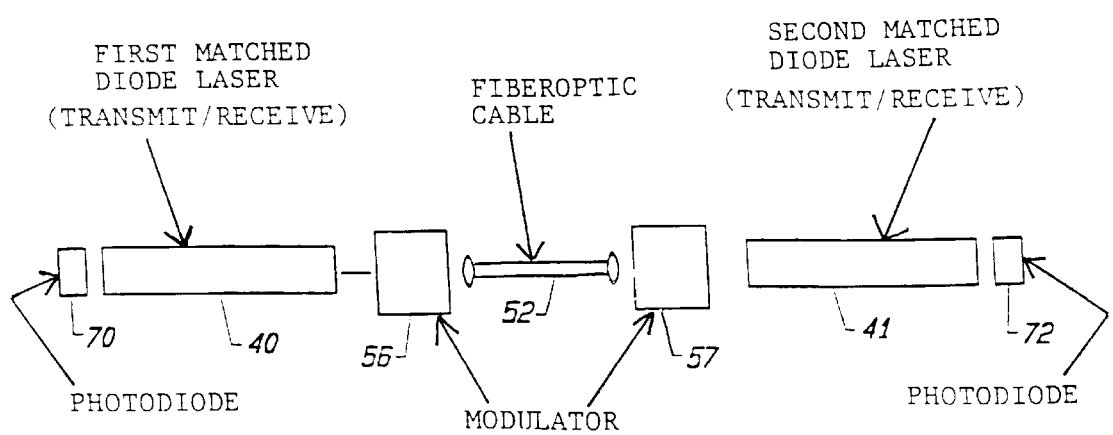
FIG. 11B is a schematic representation of first and second matched lasers coupled by a fiberoptic cable but also utilizing external electro-optic modulators.

Referring to FIGS. 11A and 11B, first and second matched lasers 40 and 41 are shown coupled by a fiberoptic cable 52. Photodiodes 70 and 72 measure the output beams of the laser cavities 40 and 41, respectively. In accordance with the present invention, the output beam of 1 or both lasers may be modulated by the "frequency injection" technique wherein a first wave frequency $f_1$ and a second wave frequency $f_2$ are used to modulate the output of either or both lasers 40 and 41. In the preferred embodiment, both lasers 40 and 41 would operate with the "frequency injection" modulated beam and would incorporate deconvolution means filtering the fundamental of $f_1$ and the second harmonic of wave $f_2$. Lasers 40 and 41 could transmit and receive bit streams simultaneously.

A similar fiberoptic network system is represented in FIG. 11B wherein external electro-optic modulators 56 and 57 are positioned between laser cavity 40 and fiberoptic cable 52 and laser cavity 41 and the other end of fiberoptic cable 52. The purpose of the external electro-optic modulators 53 and 54 is to allow modulation other than electronic modulation.

Figure 12:
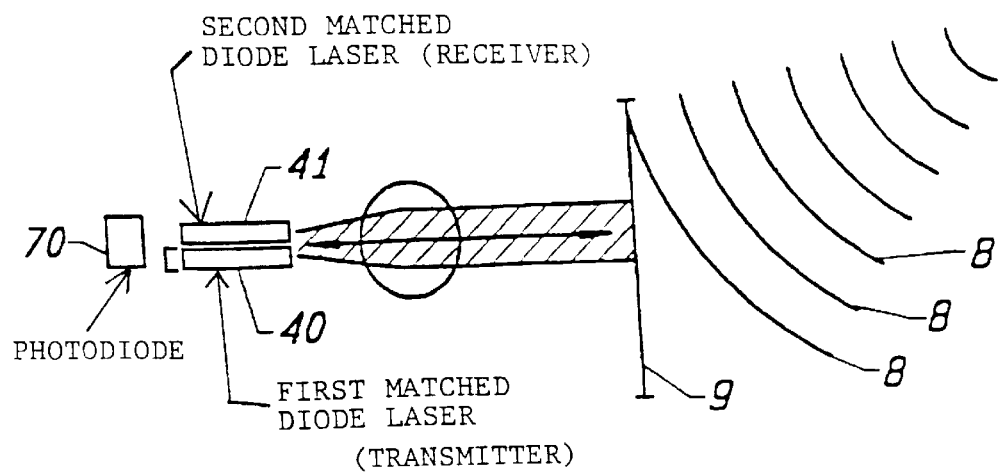
FIG. 12 is a schematic representation of a microphone utilizing the present invention.

FIG. 12 is a schematic representation of a microphone system utilizing the present invention. Sound waves 8 impact a diaphragm 9, causing the diaphragm to vibrate. The motion of the vibrating diaphragm 9 is detected by the use of matched lasers 40 and 41, wherein the output of transmitting laser 40 is directed at diaphragm 9 and the reflected laser output beam is received by laser cavity 41. The output of laser cavity 41 is measured by photodiode 70. The system shown schematically in FIG. 12 can be used with or without the "frequency injection" technique of the present invention. If the "frequency injection" technique is utilized, the necessary filters, which comprise the harmonic deconvolution means, would be connected to the photodiode 70.

Figure 13:
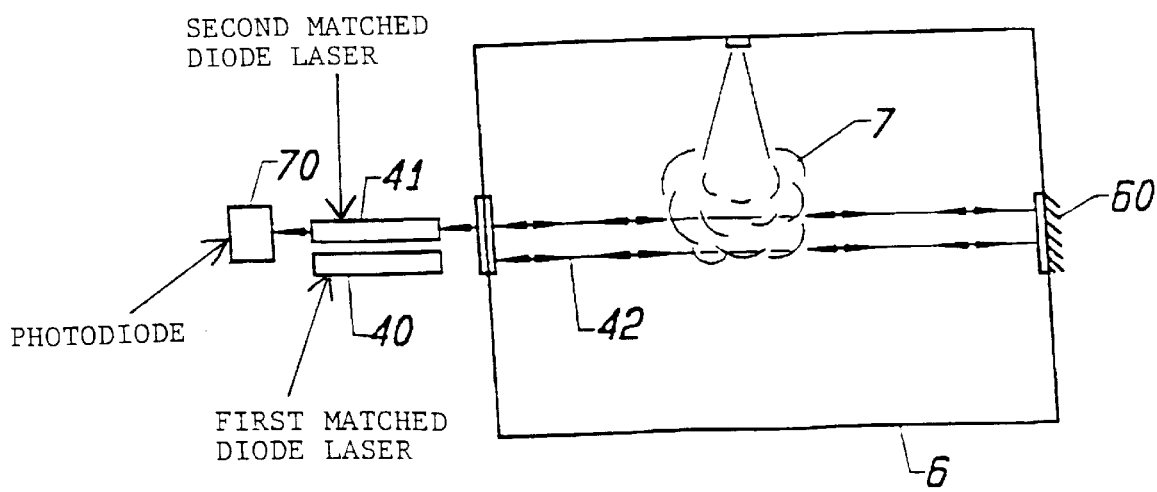
FIG. 13 is a schematic representation of a system for sensing the change of the index of refraction of a light transmitting medium according to the present invention.

FIG. 13 comprises a schematic representation of a system utilizing the present invention to sense the change of the index of refraction of a light transmitting medium. The system includes chamber 6 into which a gaseous medium 7 may be introduced which would change the index of refraction of the ambient atmosphere in the chamber 6. A pair of matched lasers 40 and 41 are mounted adjacent the chamber 6 so that the output beam of transmitting laser 40 passes through the chamber, is reflected off a mirror 60, passes back through the chamber and into the second matched laser 41 comprising the receiving laser cavity in the design shown in FIG. 13. Photodiode 70 is utilized to measure the output power of laser cavity 41. As gas 7 enters the chamber 6, the index of refraction of the material through which the laser beam is passing will change, and the phase of the laser beam entering cavity 41 will accordingly change. The phase modulation caused by the presence of gas 7 will be detected in the receiving laser cavity 41.

Figure 14:
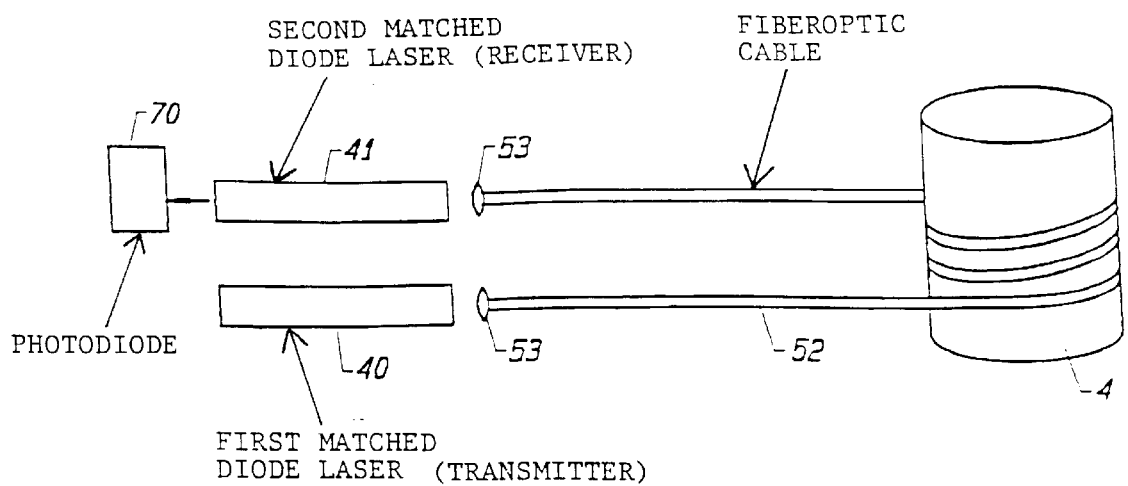
FIG. 14 is a schematic representation of a system utilizing the present invention for sensing the change in length of a fiberoptic cable.

FIG. 14 shows a system for sensing the change in length of a fiberoptic cable 52 which is wound around a member 4. As the temperature of member 4 increases, the length of fiberoptic cable 52 will be increased slightly and the change in path length will be detected by the receiving laser cavity 41. The design shown in FIG. 14 can be used with or without the "frequency injection" technique. The system shown in FIG. 14 is capable of measuring temperature and pressure changes in member 4 which could be a vessel, a pipe or any object which expands or contracts causing changes in the length of fiberoptic cable 52. In using the system shown in FIG. 14, it is ordinarily preferable to use acid-formed lenses 53 on both ends of fiberoptic cable 52.

Figure 15:
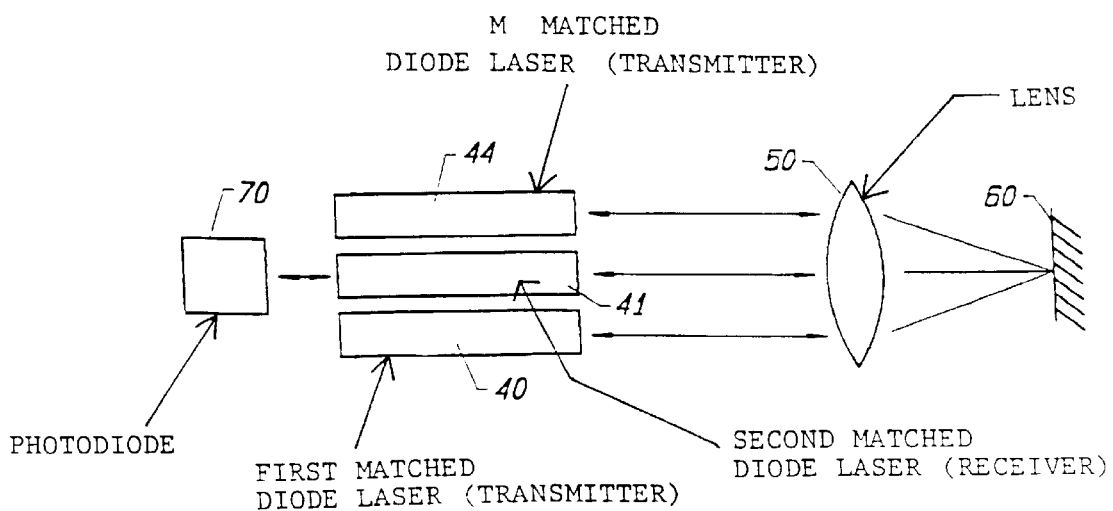
FIG. 15 is a schematic representation wherein multiple matched lasers are utilized according to the present invention.

FIG. 15 is a schematic representation of another form of the invention wherein multiple matched lasers 40,41,42 are utilized. It is understood that the concept of the invention would work with larger combinations of matched lasers than the three shown in FIG. 15. The invention includes arrays of m matched transmitting lasers wherein the output beam of each laser may be modulated with a complex wave form and n receiving matched lasers. For example, eight matched lasers could be used wherein five of the lasers are transmitting lasers and the middle three lasers would be receiving lasers. The advantage of using multiple matched lasers is to be able to electronically extrapolate higher resolution data.

Figure 16:
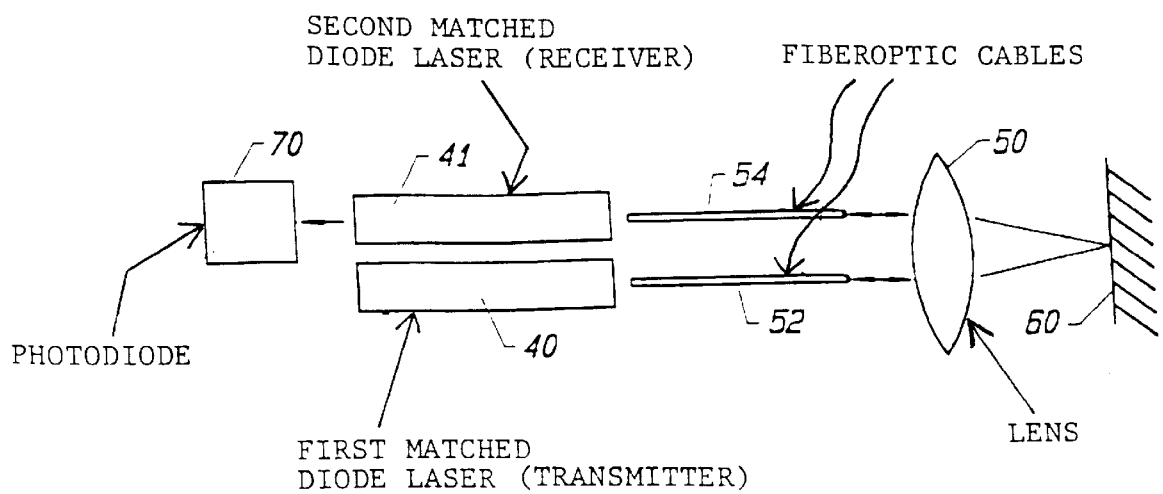
FIG. 16 is a schematic representation of another embodiment of the invention wherein fiberoptic cables are used in transmitting the output and reflected beam.

FIG. 16 shows another embodiment of the invention wherein fiberoptic cables 52 and 54 are utilized to transmit the output beam of transmitting laser 40 to lens 50 and to transmit the reflected beam from lens 50 to receiving laser cavity 41. It is understood that the lens 50, shown in FIG. 16, could be deleted from the design if acid formed lenses were formed on the ends of fiberoptic cables 52 and 54 which are adjacent lens 50 in FIG. 16.

FIGS. 17A, 17B and 17C show examples of line width curves of "matched lasers" to illustrate the meaning of that phase.

Figure 18:
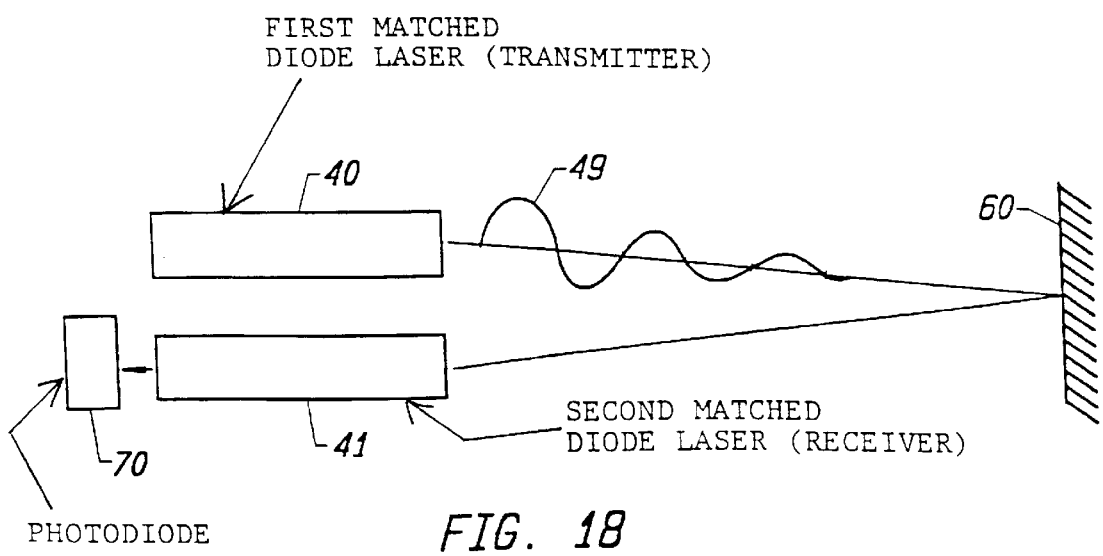
FIG. 18 is a schematic representation of an embodiment of the present invention utilizing beam amplitude modulation with limited coherence length.

FIG. 18 illustrates a beam amplitude modulation scheme for determining the position of a reflective target surface. The embodiment shown in FIG. 18 utilizes matched lasers 40 and 41 which represents the preferred embodiment for amplitude modulation. As shown by the schematic representation of the beam pattern 49, the coherence length of the output beam is reduced intentionally by applying a rather strong RF signal to modulate laser 40 and to dissipate the coherence of the beam in order to "flatten" the phase response of the reflected beam entering the receiving laser cavity 41. As the amplitude of the output beam of laser 40 varies, the amplitude of the output beam of the receiving laser cavity 41 sensed by photodiode 70 will also rise and fall in time-dependent fashion. The change in amplitude is utilized to derive positional information regarding the target. The system, shown in FIG. 18 for amplitude modulation, could be operated with a single laser cavity, although that embodiment would not function as well as the matched laser system shown in FIG. 18.

Figure 19:
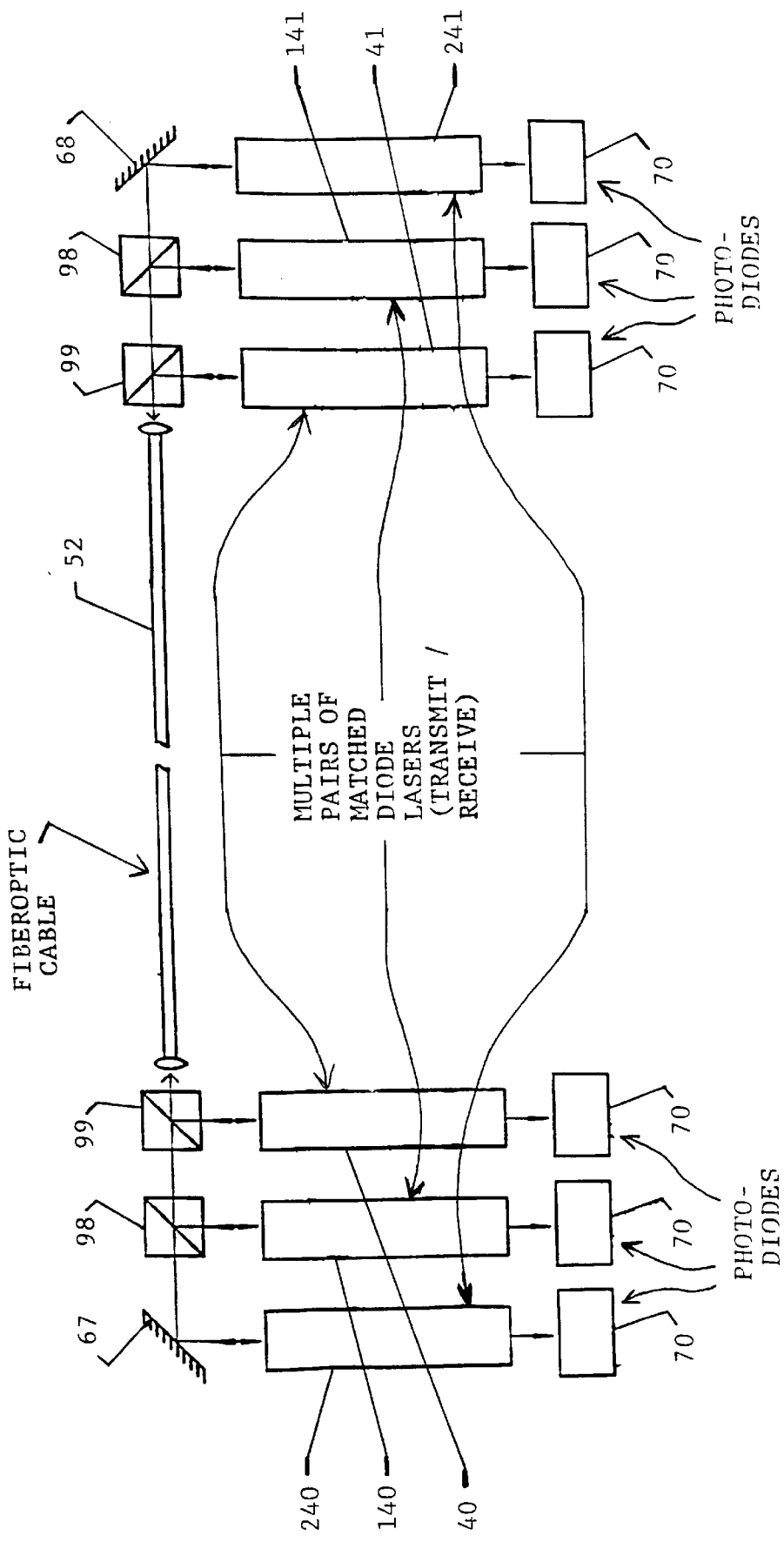
FIG. 19 is a schematic representation of a fiberoptic system according to the present invention in which multiplexing of the signal is facilitated.

FIG. 19 shows a fiberoptic system in which multiplexing of the signal is facilitated by the use of multiple sets of matched lasers. Lasers 40 and 41 are matched. Lasers 140 and 141 are matched but at a different wavelength. Lasers 140 and 141 will not resonate at a common frequency with either of lasers 40 or 41. A third set of matched lasers 240 and 241 is also provided. Lasers 240 and 241 are matched with each other but, again, are not matched with any of lasers 40,41 or 140,141. The purpose of matching multiple lasers in this fashion is to allow for simultaneous transmission of bit streams bidirectionally through fiberoptic cable 52. A big stream transmitted from laser 40 will be received only by laser 41, whereas a bit stream transmitted by laser 140 through the same fiberoptic cable 52 will only be received by its matched laser 141. The output from the lasers may be easily introduced into fiberoptic cable 52 by beam splitters 98,99 and by mirrors 67 and 68. Photodiodes 70 measure the output power of each receiving cavity, the variation in the output power forming the transmitted bit stream.

Figure 20A:
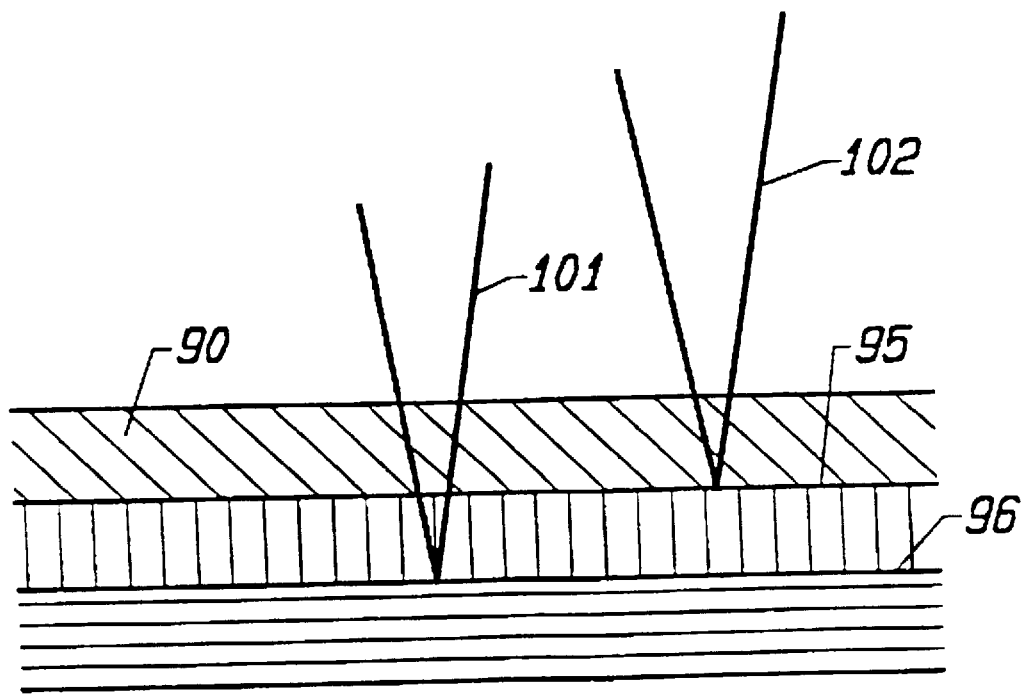
FIGS. 20A and 20B are sectional views of transparent discs for use with the present invention.
Figure 20B:
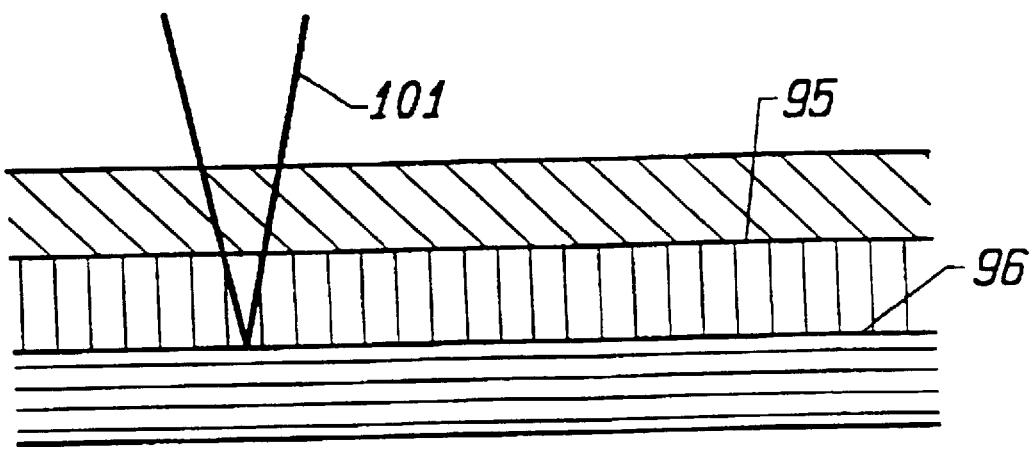

FIGS. 20A and 20B represent the use of multiple layer optical discs wherein each layer is read independently of the other. For example, upper layer 95 and lower layer 96 may have pits formed therein. For clarity, the individual pits are not shown in FIG. 20. FIG. 20A shows a pair of laser beams 101 and 102 being simultaneously focused at different depths on disc 90, so that laser output beam 101 is reading the pits along layer 96 and focused output beam 102 is simultaneously reading the pits at layer 95. Alternately, as shown in FIG. 20B, laser output beam 101 may be used individually to scan the pits in layer 96.

Figure 21:
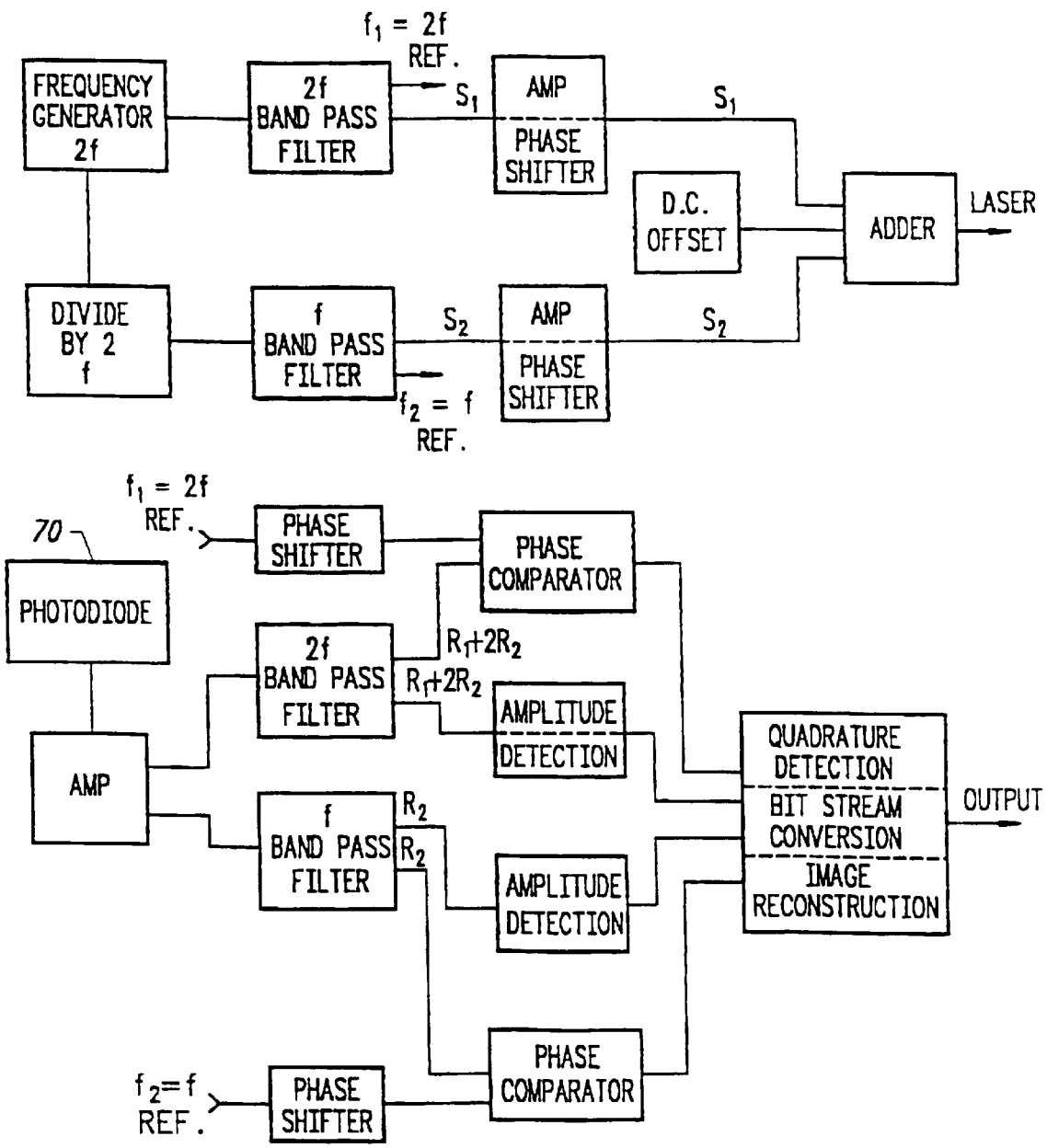
FIG. 21 is a schematic representation of one form of drive and receiving electronics which may be used with the present invention.

FIG. 21 is a schematic representation of the drive and receive electronics that may be used in one embodiment of the invention. The specific relationship of modulating signal $f_1$ to $f_2$ is $f_1=2f_2$. A frequency generator generates a 2f signal which passes through a bandpass filter, resulting in reference signal $S_1$. Signal f may be generated by dividing the 2f signal, passing it through a bandpass filter resulting in input reference signal $S_2$. Input reference signals $S_1$ and $S_2$ are amplified and added to a DC offset signal which is typically 1.5 volts. The reference signals are then applied to the laser.

The lower portion of the schematic shown in FIG. 21 illustrates the deconvolution electronics of the present invention and includes a photodiode 70, the output of which is amplified and passed through a bandpass filter for the 2f signal and a separate bandpass filter for the f signal. The outputs are then entered into a phase comparator which compares the phase of input reference signal $f_1$ with the phase of $R_1+2R_2$. The output of the f bandpass filter is $R_2$ which is entered into phase comparator to compare the phase of $R_2$ with $S_2$. These comparisons form the basis of the quadrature detection scheme according to the present invention.

Figure 22:
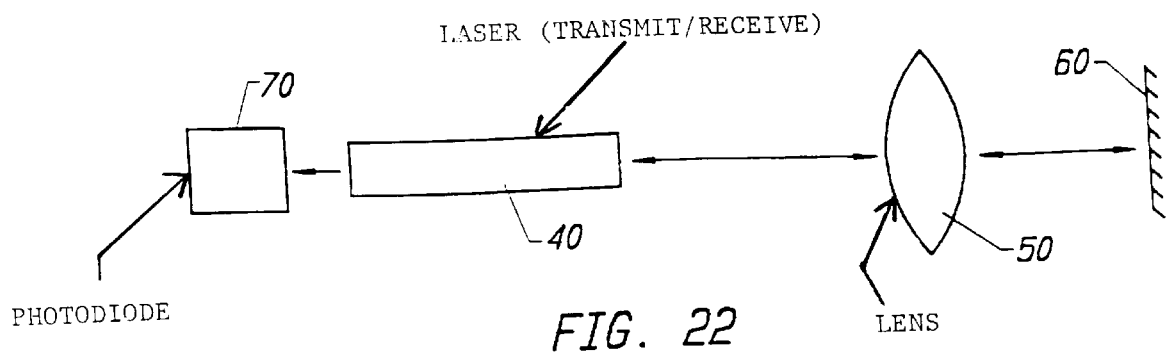
FIG. 22 is a schematic representation illustrating how the present invention may be used in conjunction with a single laser cavity.

FIG. 22 is a schematic representation of yet another embodiment of the present invention wherein a single laser 40 is utilized as both the transmitting and receiving laser using the "frequency injection" technique and harmonic deconvolution means of the present invention. The schematic shown in FIG. 22 may be used in target motion detection.

FIG. 23 is a schematic representation of matched diode lasers 40 and 41, wherein no photodiode and no focusing lens are required to determine the position of target 60. The output of diode laser 40 is electronically modulated. The output beam is scattered off the target or mirror 60 with a portion being reflected into receiving laser cavity 41. The impedance of receiving diode laser 41 is measured, and time-dependent changes in impedance are used to derive positional information of the target 60.

The invention described above may be used in a variety of end uses. In addition to the end uses discussed above in the application, the invention may be used in a laser micrometer device. This would be a rather inexpensive device for measuring micromotion bidirectionally.

The invention as described above could also readily be used for a variety of pressure and vacuum sensors. Such a device could utilize a diaphragm for sensing pressure or vacuum and the motion of the diaphragm could be readily detected by the embodiments disclosed above.

Another end use of the invention described herein is a robotic sensing device which could be used in conjunction with a variety of robotic elements to assist in tracking the precise location of one or more robotic elements.

The present invention could also be used as a thermometer by sensing the thermal-expansion of a variety of metals or ceramics.

The invention can also be utilized to measure the thickness of electroplating material being applied to a substrate. The device could be mounted in the electroplating chamber. The invention can also be used to measure the thickness of molecular deposition such as used on optical lenses.

The amplitude modulation technique of the present invention could also be used to read high speed optical tape. The amplitude modulation technique of the present invention could also be used as a bar code reader.

The present invention can also be utilized in conjunction with scanners and facsimile machines.

What is claimed is:

1. Apparatus for transmitting a bit stream of information between first and second stations, comprising:

a first of two matched diode lasers located at said first station for producing a first stable-resonator laser output beam of coherent light;

a second of said two matched diode lasers located at said second station for producing a second stable-resonator laser output beam of coherent light;

fiberoptic cable means connecting said two matched lasers;

means for applying a bit stream onto said first diode laser output beam;

said second matched diode laser forming a receiving cavity means for receiving said first output beam carrying said bit stream;

means for measuring the power of said second matched diode laser output beam; and means for using time-dependent changes in the measured output power of said second matched diode laser output beam to read said bit stream.

2. The apparatus of claim 1 further comprising:

beam modulation means for inducing a compound modulated beam pattern onto said first output beam, comprising a first wave of frequency $f_1$ and a second wave of frequency $f_2$, and wherein fundamental and harmonic waves of waves $f_1$ and $f_2$ are generated in said receiving laser cavity means; and deconvolution means connected to said measuring means for filtering the fundamental frequency of wave $f_1$ and a selected one of the harmonics of wave $f_2$ and using time-dependent changes in the measured power of said second matched diode laser output beam to read said bit stream.

3. The apparatus of claim 2 wherein said bit stream is applied to said compound modulated beam using a base three format and wherein $\lambda$ is the wavelength of said output beam of coherent light and wherein the phase of either said fundamental of wave $f_1$ or the phase of said second harmonic of wave $f_2$ changes 180° four times every $\lambda$ relative to a reference signal, and wherein said deconvolution means comprises:

phase quadrature detection means connected to said measuring means for detecting said phase change every $\lambda/4$ of either said fundamental wave or said second harmonic wave and using said phase quadrature information and amplitude information to read said bit stream with base three format.

4. The apparatus of claim 1 for transmitting two bit streams bi-directionally between said first and second matched diode lasers, further comprising:

means for applying a second bit stream onto said second laser output beam;

said first diode laser forming a second receiving laser cavity means for receiving said second laser output beam carrying said second bit stream;

means for measuring the power of said first matched diode laser output beam; and means for using time-dependent changes in the measured output power of said first matched diode laser output beam to read said second bit stream.

5. Apparatus for transmitting multiple bit streams of information between first and second stations, comprising:

n sets of matched diode lasers, each of said n sets having a first and second diode laser, and each of said n sets operating at different wavelengths;

said first of said n matched diode lasers located at said first station for producing n first stable-resonator laser output beams of coherent light of n different wavelengths;

said second of said n matched diode lasers located at said second station for producing n second stable-resonator laser output beams of coherent light of n different wavelengths;

fiberoptic cable means connecting said n sets of matched lasers;

means for applying n different bit streams onto said n first laser output beams, a different bit stream being applied to each of said n first laser output beams;

said second of said n matched diode lasers forming n receiving laser cavity means for receiving said n first laser output beams;

means for measuring the power of said n second matched diode laser output beams; and means for using time-dependent changes in the measured output power of said n second matched diode laser output beams to read said n bit streams.

6. The apparatus of claim 5 further comprising:

beam modulation means for inducing a compound modulated beam pattern onto each of said output beams of said n first matched diode lasers, comprising a first wave of frequency $f_1$ and a second wave of frequency $f_2$, and wherein fundamental and harmonic waves of waves $f_1$ and $f_2$ are generated in each of said n receiving laser cavity means; and deconvolution means connected to said measuring means for filtering the fundamental frequency of wave $f_1$ and a selected one of the harmonics of wave $f_2$ and using time-dependent changes in the measured power of said output beam in each of said n second matched lasers to read each of the n bit streams being transmitted.

7. The apparatus of claim 5 wherein said multiple bit streams are transmitted from said first station simultaneously and received at said second station simultaneously.

* * * * *